US012213577B1

(12) United States Patent
Lopez et al.

(10) Patent No.: US 12,213,577 B1
(45) Date of Patent: Feb. 4, 2025

(54) COMBINED WEIGHTLIFTING BELT AND STORAGE PACK

(71) Applicants: Ashley Lopez, Portland, OR (US); Braiddey Ruzicka, Beaverton, OR (US); Malyna Sanchez, Manteca, CA (US); Matthew Hsu, Portland, OR (US); Yi Chen Yeh, Portland, OR (US); Barry Phothong, Portland, OR (US)

(72) Inventors: Ashley Lopez, Portland, OR (US); Braiddey Ruzicka, Beaverton, OR (US); Malyna Sanchez, Manteca, CA (US); Matthew Hsu, Portland, OR (US); Yi Chen Yeh, Portland, OR (US); Barry Phothong, Portland, OR (US)

( * ) Notice: Subject to any disclaimer, the term of this patent is extended or adjusted under 35 U.S.C. 154(b) by 225 days.

(21) Appl. No.: 17/750,788

(22) Filed: May 23, 2022

Related U.S. Application Data (60) Provisional application No. 63/191,502, filed on May 21, 2021.

(51) Int. Cl.
*A45F 3/00* (2006.01)
*A45F 3/02* (2006.01)
*A61F 5/28* (2006.01)

(52) U.S. Cl.
CPC .............. *A45F 3/02* (2013.01); *A45F 3/005* (2013.01); *A61F 5/28* (2013.01)

(58) Field of Classification Search
CPC ........ A45F 3/02; A45F 3/005; A63B 2225/68; A63B 21/4009; A61F 5/028

USPC ........................................ 224/660, 662, 664
See application file for complete search history.

(56) References Cited

U.S. PATENT DOCUMENTS

| | | | | |
|---|---|---|---|---|
| 2,449,641 | A | * | 9/1948 | Cidissen ................... A61F 5/03 128/96.1 |
| D238,725 | S | * | 2/1976 | Zerobnick ...................... D3/226 |
| 4,384,372 | A | * | 5/1983 | Rector ................... A41F 9/002 224/684 |
| 4,475,543 | A | * | 10/1984 | Brooks ................... A61F 5/028 602/19 |
| 4,685,668 | A | | 8/1987 | Newlin, Jr. |
| 4,745,911 | A | | 5/1988 | Bender |
| 4,802,667 | A | | 2/1989 | Altner |
| 4,899,887 | A | | 2/1990 | Cachero |
| 4,944,509 | A | | 7/1990 | Snider |
| 4,964,401 | A | | 10/1990 | Taigen |
| 5,105,806 | A | * | 4/1992 | Woodhouse ............ A61F 5/028 128/112.1 |
| D335,025 | S | | 4/1993 | Thomas |
| 5,228,609 | A | * | 7/1993 | Gregory ................... A45F 3/02 224/907 |

(Continued)

*Primary Examiner* — Justin M Larson
(74) *Attorney, Agent, or Firm* — Cramer Patent & Design, PLLC.; Aaron R. Cramer (57) ABSTRACT

A combined support belt and storage pack is a multi-purpose weightlifting belt having adjustable foam fill, an ergonomic back panel, a dual clip adjustment system, a storage pack and abdominal strap. When used as a weightlifting belt the storage pack is removed and the abdominal strap is utilized to secure about the waist of a user via the dual clip adjustment system. When not in use as a weightlifting belt, the device may operate as a shoulder pack having the storage pack secured to the ergonomic back and abdominal strap.

5 Claims, 5 Drawing Sheets

(56) References Cited

U.S. PATENT DOCUMENTS

| | | | | |
|---|---|---|---|---|
| 5,232,424 A | | 8/1993 | Pearson et al. | |
| 5,240,156 A | * | 8/1993 | Sicotte | A45F 5/02 224/583 |
| 5,374,919 A | * | 12/1994 | Zelka | G08B 15/004 224/664 |
| D358,215 S | * | 5/1995 | Reed | D24/190 |
| D375,823 S | * | 11/1996 | Bleiweis | D29/101.5 |
| 5,693,006 A | * | 12/1997 | Slautterback | A61F 5/028 224/675 |
| 5,727,720 A | * | 3/1998 | Thatcher | A45F 3/00 224/582 |
| 6,364,186 B1 | * | 4/2002 | Gilmour | A45F 3/02 224/660 |
| 6,610,022 B1 | | 8/2003 | Ashbaugh et al. | |
| 6,666,838 B2 | * | 12/2003 | Modglin | A61F 5/028 128/100.1 |
| 6,681,974 B2 | * | 1/2004 | Rotter | A45F 4/02 224/680 |
| 6,698,636 B2 | * | 3/2004 | Angus | A45F 3/12 224/660 |
| D497,715 S | * | 11/2004 | Saltarelli | D3/226 |
| 7,201,299 B2 | * | 4/2007 | Forsman | A45F 3/14 224/148.2 |
| 7,329,231 B2 | * | 2/2008 | Frank | A61F 5/028 602/19 |
| 7,364,558 B2 | * | 4/2008 | Weaver, II | A61F 5/028 602/19 |
| D695,008 S | * | 12/2013 | Pomerantz | D3/221 |
| 9,437,175 B2 | * | 9/2016 | Sumner | G10D 13/02 |
| D789,546 S | * | 6/2017 | Matfus | D24/190 |
| D809,288 S | * | 2/2018 | Preseren | D3/226 |
| 9,901,160 B2 | * | 2/2018 | Donato, Jr. | A45F 5/021 |
| 9,931,532 B2 | | 4/2018 | Castaneda | |
| D839,591 S | * | 2/2019 | Yamanaka | D3/226 |
| D863,756 S | * | 10/2019 | Chudy | D3/226 |
| D869,578 S | * | 12/2019 | Voigt | D21/662 |
| D880,851 S | * | 4/2020 | Liu | D3/224 |
| D912,397 S | * | 3/2021 | Rui | D3/221 |
| D975,437 S | * | 1/2023 | Liu | D3/226 |

\* cited by examiner

COMBINED WEIGHTLIFTING BELT AND STORAGE PACK

RELATED APPLICATIONS

The present invention is a continuation of U.S. Provisional Application No. 63/191,502 filed on May 21, 2021, the entire disclosures of which are incorporated herein by reference.

FIELD OF THE INVENTION

The present invention relates generally to a combined support belt and storage pack commonly used in weightlifting.

BACKGROUND OF THE INVENTION

When engaging in a weightlifting activity, there are many things to consider when it comes to safety. Certain aspects of weightlifting can induce stress and fatigue to certain areas of the body. Overdoing certain activities, such as continual straining, quick jerking movement, and using heavy loads among other activities, can lead to injury. Therefore, the use of supporting elements can greatly impact the health and safety of the weightlifter. Such a supporting element is a weightlifter's belt.

The weightlifter's belt aids in supporting the abdomen region of the weightlifter when engaging in lifting and training with heavy loads. The weightlifter's belt is especially good in supporting the core muscles when lifting weights but is commonly not used or forgotten about because it can be uncomfortable at times to wear, because it needs constant adjustment during a single training session, and because it is not fashionable, among other reasons.

Weightlifters also carry a lot of equipment during a training session, such as towels, water bottles, chalk, or other ancillary items. It is a hassle to carry all of this equipment as well as a weightlifter's belt, when travelling to and from training. Therefore, it has been identified that a need exists to combine the functionality of a weightlifter's belt that addresses and fixes the problems associated with use, as well as a carrying tote to transport essential and desired items in a single device. Thus, the present invention fulfills this need.

SUMMARY OF THE INVENTION

The principles of the present invention provide for a weightlifting belt and shoulder pack assembly having a pack which has a panel and a pouch, an abdominal plate which has a semi-rigid pad, the abdominal plate is coupled to the pack, a strap which has a strip of flexible non-elastic material, a left buckle which is adapted to couple the strap to the pack on a left side of a user—the left buckle includes a male buckle component and a female buckle component, and a right buckle which is adapted to couple the strap to the pack on a right side of the user—the right buckle includes a male buckle component and a female buckle component.

The panel may serve as a backing and includes a plurality of extension wings that extend laterally beyond the pack. The extension wings may be adapted to flex such that the extension wings wrap partially around a torso of the user. The pouch may be a flexible bag removably coupled to the panel. The pouch may be hollow and may hold a foam support and the one or more items being carried. The foam support may be inserted into and removed from the contact side pocket via a contact side aperture to cushion the user. The contact side aperture may be closed using a contact side fastener to prevent the foam support from sliding out of the pack.

The weightlifting belt and shoulder pack assembly may further comprise a first pack strap having a first pack strap adjuster extending away from a first end of the pouch and a second pack strap having a second pack strap adjuster extending away from a second end of the pouch. The first pack strap and second pack strap are removable attached to the abdominal plate. The pack may be a contact side pocket. The contact side pocket may be accessible from the contact side of the pack via a contact side aperture when the pack is not being worn. A front strap of webbing material may be affixed to a front surface of the storage pocket to enable retention of a piece of auxiliary equipment for storage or transport.

The abdominal plate may be adapted to be pressed against an abdomen of a torso front of the user with the pack pressing against a lower torso back of the user and the strap passing above a hip bone of the user. The abdominal plate may be adapted to press against a chest of the user with the pack resting against a shoulder blade and the strap passing over one shoulder and under an opposing arm of the user.

The strap may be made of nylon webbing. The strap may detachably couple to the pack via the left buckle and the right buckle. The left buckle of the male buckle component may be inserted into a mating aperture on the female buckle component where one or more release tabs on the male buckle component to engage with one or more release apertures on the female buckle component to prevent the male buckle component and the female buckle component from releasing. The left buckle of the male buckle component may be detached by applying external pressure to the one or more release tabs and pulling the male buckle component and the female buckle component apart.

The right buckle of the male buckle component may be inserted into a mating aperture on the female buckle component where one or more release tabs on the male buckle component to engage with one or more release apertures on the female buckle component to prevent the male buckle component and the female buckle component from releasing. The right buckle of the male buckle component may be detached by applying external pressure to the one or more release tabs and pulling the male buckle component and the female buckle component apart.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY 100 weightlifting belt and shoulder pack assembly
200 pack
202 panel
204 extension wing
210 pouch
220 contact side pocket
222 contact side aperture
224 contact side fastener
226 foam support
230 storage pocket
232 storage aperture
234 storage fastener
236 front strap
240 abdominal plate
242 strap retainer
244 first pack strap
245 second pack strap
248 first pack strap adjuster
249 second pack strap adjuster
252 strap
254 left buckle
256 right buckle
260 male buckle component
264 release tab
270 female buckle component
274 mating aperture
276 release aperture
278 webbing slot
282 webbing slider
284 loop
290 contact side
292 non-contact side
A arm
B torso back
C chest
F torso front
S shoulder
U user

DESCRIPTION OF THE INVENTION

The present invention is directed to a weightlifting belt and shoulder pack assembly (herein described as the "invention") 100. The invention 100 may comprise a pack 200, an abdominal plate 240, a strap 252, a left buckle 254, and a right buckle 256. The invention 100 may be adapted to be worn as a weightlifting belt around a torso B, F of a user U to brace the core of a user U while lifting weights. The invention 100 may be adapted to be worn as a shoulder pack over a shoulder S of a user U to carry one (1) or more items within the pack 200. When worn as the weightlifting belt, the abdominal plate 240 may be adapted to press against the abdomen of the torso front F of a user U with the pack 200 pressing against a lower torso back B of a user U and the strap 252 passing above a hip bone of a user U. When worn as the shoulder pack, the abdominal plate 240 may be adapted to press against a chest C of a user U with the pack 200 resting against a shoulder blade and the strap 252 passing over one (1) shoulder S and under the opposing arm A of a user U.

Both the pack 200 and the abdominal plate 240 may be defined by a contact side 290 and a non-contact side 292. The contact side 290 may be positioned to contact the user U when the invention 100 is in use. The non-contact side 292 may be opposite the contact side 290 (i.e., away from the user U).

The pack 200 may comprise a panel 202 and a pouch 210. The pack 200 may be adapted to cushion the lower torso back B when used as the weightlifting belt and may provide storage space when used as the shoulder pack. The panel 202 may be a backing for the pack 200. The panel 202 may be located on the contact side 290 of the pack 200. In some embodiments, the panel 202 may comprise extension wings 204 that extend laterally beyond the pack 200. The extension wings 204 may be adapted to flex such that the extension wings 204 wrap partially around the torso B, F of the user U.

The pouch 210 may be a flexible bag removably coupled to the panel 202. The pouch 210 may be hollow and may be operable to hold a foam support 226 and the one (1) or more items being carried. Extending away from a first end of the pouch 210 is a first pack strap 244, having a first pack strap adjuster 245 thereon. Extending away from a second end of the pouch 210 is a second pack strap 248, having a second pack strap adjuster 249 thereon. The first pack strap 244 and second pack strap 249 may be capable of removable attachment to a feature on the abdominal plate 240.

The pack 200 may comprise a contact side pocket 220 (i.e., the rear side of the panel 202). The contact side pocket 220 may be accessible from the contact side 290 of the pack 200 via a contact side aperture 222 when the pack 200 is not being worn. The foam support 226 may be inserted into and removed from the contact side pocket 220 via the contact side aperture 222. The contact side aperture 222 may be closed using a contact side fastener 224 to prevent the foam support 226 from sliding out of the pack 200. The foam support 226 may be operable to cushion the lower torso back B of a user U. The foam support 226 may be removed from the pack 200 and replaced by a replacement foam support when necessitated by wear.

The pouch 210 may comprise one (1) or more storage pockets 230. An individual storage pocket selected from the one (1) or more storage pockets 230 may be accessible from the non-contact side 292 of the pack 200 (e.g., the front of the pouch 210) via a storage aperture 232. The one (1) or more items may be inserted into and removed from an individual storage pocket 230 via the storage aperture 232. The storage aperture 232 may be closed using a storage fastener 234 to prevent the items from sliding out of the pack 200. A front strap 236 of webbing material is affixed or otherwise attached to a front surface of the storage pocket 230 to enable retention of auxiliary equipment for storage or transport, such as carabiners holding a water bottle, etc. The front strap 236 can be configured into a set of individual segments of identical or different sizes, each fashioned as a loop as in the exemplary embodiment.

In some embodiments, the contact side fastener 224, the storage fasteners 234, or combinations thereof may be zippers. The internal cavities where the foam support 226 and the items reside may be separate cavities.

The abdominal plate 240 may be a semi-rigid pad. The abdominal plate 240 may be adapted to press against the abdomen of the torso front F of a user U to brace the core through intra-abdominal pressure during use as the weightlifting belt. The abdominal plate 240 may be held in place by the strap 252. The strap 252 may pass through a pair of strap retainers 242 on the abdominal plate 240 to retain the strap 252 on the abdominal plate 240.

The strap 252 may be a strip of flexible non-elastic material. As a non-limiting example, the strap 252 may be made of nylon webbing. The strap 252 may detachably couple to the pack 200 via the left buckle 254 and the right buckle 256. The strap 252 may be adapted to encircle the torso B, F of a user U to hold the abdominal plate 240 in position at the torso front F of a user U and to hold the pack 200 in position at the torso back B of a user U.

The left buckle 254 may be adapted to couple the strap 252 to the pack 200 on the left side of a user U. The right buckle 256 may be adapted to couple the strap 252 to the pack 200 on the right side of the user U.

An individual buckle selected from the left buckle 254 and the right buckle 256 may comprise a male buckle component 260 and a female buckle component 270. The male buckle component 260 may be inserted into a mating aperture 274 on the female buckle component 270 where one (1) or more release tabs 264 on the male buckle component 260 may engage with one (1) or more release apertures 276 on the female buckle component 270 to prevent the male buckle component 260 and the female buckle component 270 from releasing. The individual buckle may be detached by applying external pressure to the one (1) or more release tabs 264 and pulling the male buckle component 260 and the female buckle component 270 apart.

The male buckle component 260 and the female buckle component 270 may comprise one (1) or more webbing slots 278. The strap 252 may couple to the webbing slots 278. In general, if a coupling between the strap 252 and the individual buckle is to be non-adjustable, the webbing slots 278 at that coupling may comprise a single slot which the strap 252 may pass through before the strap 252 is stitched to itself. If the coupling between the strap 252 and the individual buckle is to be adjustable, the webbing slots 278 at that coupling may comprise two (2) or more slots which the strap 252 may zigzag through while making a one hundred eighty degree) (180° turn. For the non-adjustable coupling, the strap 252 will not be stitched to itself but instead will be free to slide through the webbing slots 278.

In a preferred embodiment, the left buckle 254 and the right buckle 256 may be side-release buckles where two (2) release tabs on the side of the male buckle component 260 engage two (2) release apertures on the side of the female buckle component 270 to lock the buckle halves together.

In some embodiments, the strap 252 may comprise one (1) or more webbing sliders 282. The webbing sliders 282 may capture the captive end of the strap 252 and the free end of the strap 252 after the strap 252 has passed through the female buckle component 270 or the male buckle component 260 and made a one hundred eighty degree) (180° turn. The webbing sliders 282 may retain the free end of the strap 252 to prevent the free end of the strap 252 from interfering with usage of the invention 100.

In some embodiments, a loop 284 of webbing material may be coupled to the top of the pack 200 so that the pack 200 may be hung on a hook when stored.

In a preferred embodiment, the male buckle component 260 of the left buckle 254 is coupled to the left side of the pack 200 and the female buckle component 270 of the right buckle 256 is coupled to the right side of the pack 200. In a preferred embodiment, the strap 252 may comprise the female buckle component 270 at one (1) end and the male buckle component 260 at the opposing end such that the female buckle component 270 of the strap 252 may mate with the male buckle component 260 of the pack 200 and the male buckle component 260 of the strap 252 may mate with the female buckle component 270 of the pack 200.

In a preferred embodiment, the male buckle component 260 and the female buckle component 270 that are coupled to the pack 200 may be non-adjustably coupled to the pack 200 via sections of webbing. The female buckle component 270 and the male buckle component 260 that are coupled to the strap 252 may be adjustably coupled to the strap 252 such that the length of the strap 252 may be modified by repositioning the female buckle component 270, the male buckle component 260, or both.

Those skilled in the art will recognize that the genders and sides associated with placement of the male buckle components 260 and the female buckle components 270 may be modified without departing from the scope and spirit of the invention 100.

Figure 6:
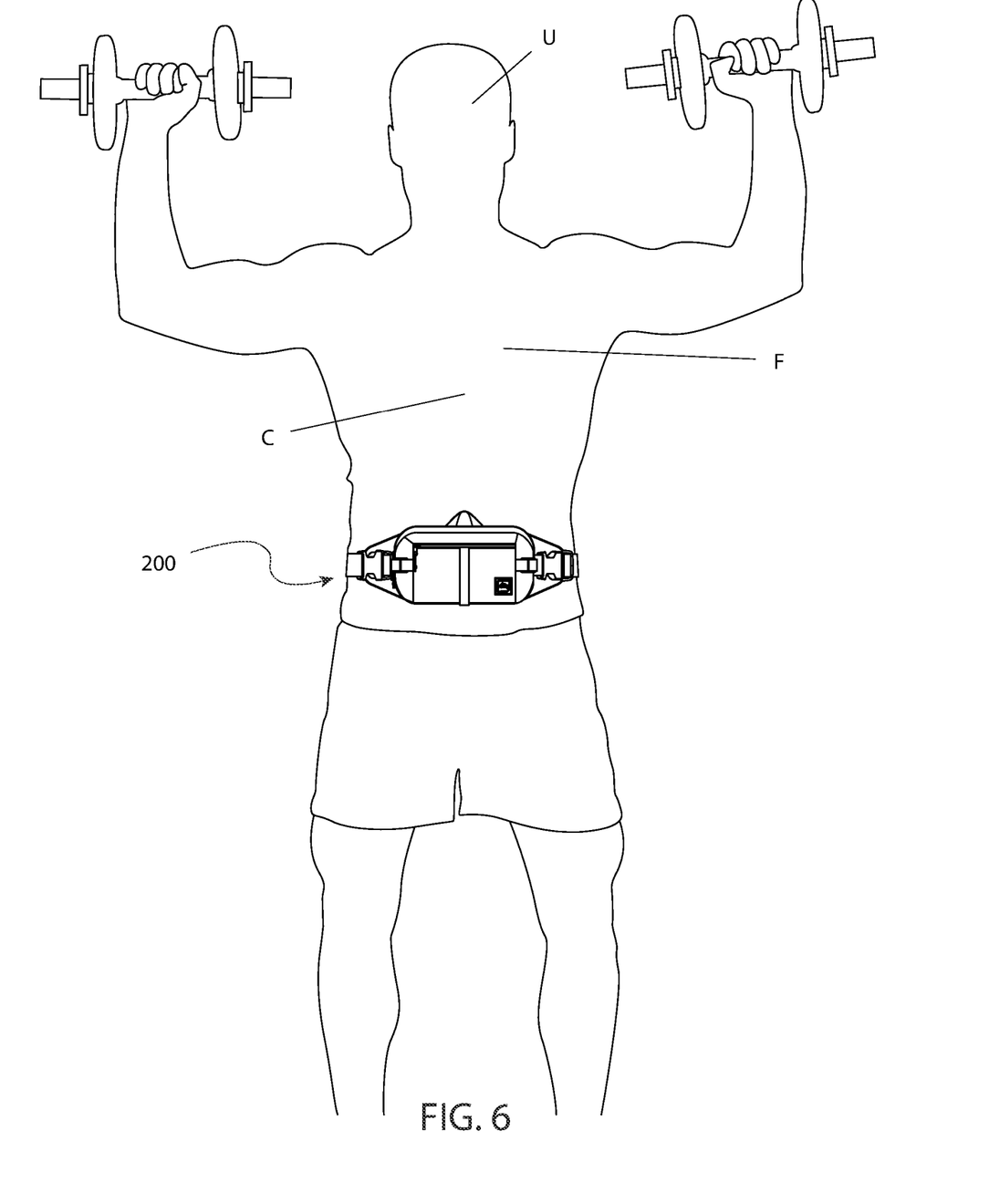
FIG. 6 is a first environmental view of an abdominal plate and a strap; and, FIG. 7 is a second environmental view of an abdominal plate and strap.
Figure 7:
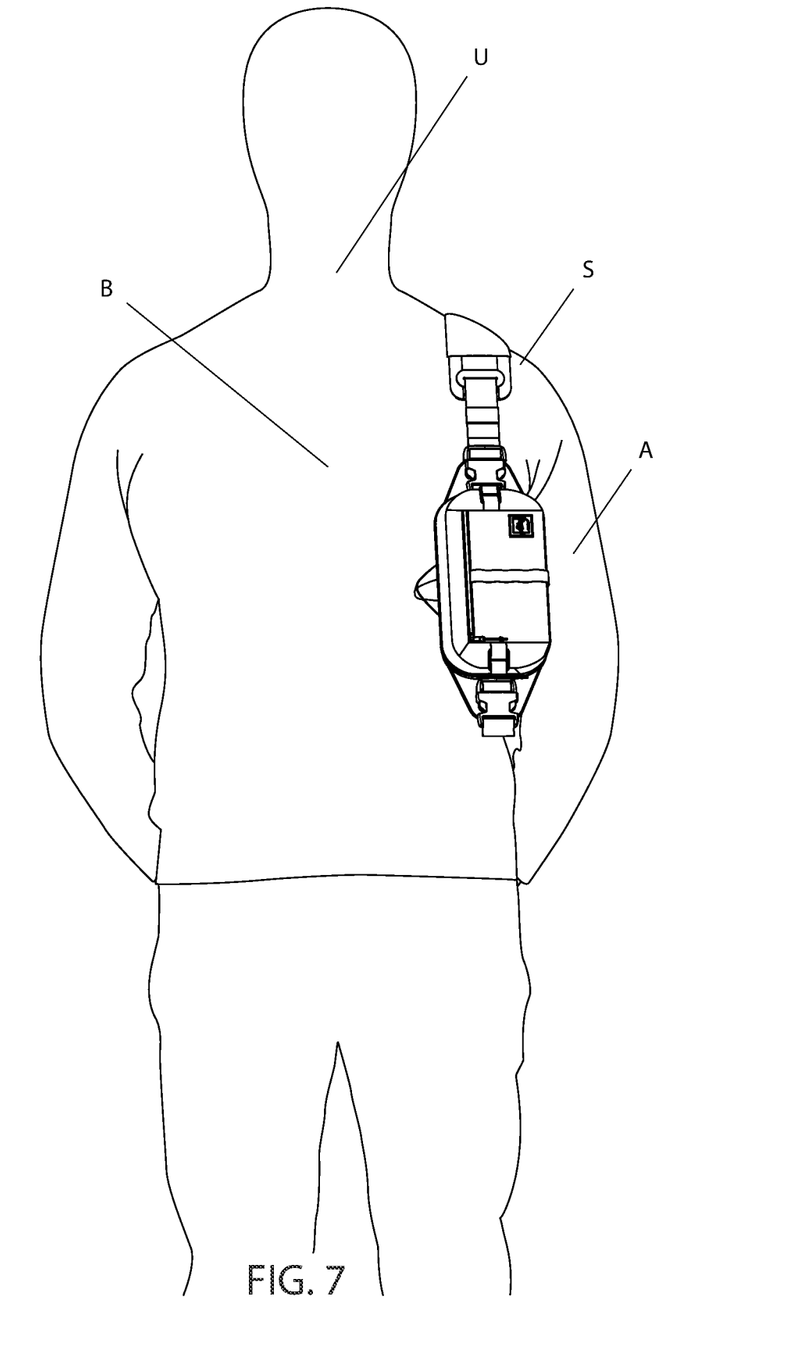

The invention 100 may be used as a weightlifting belt (as illustrated in FIG. 6) or as a shoulder pack (as illustrated in FIG. 7). To use the invention 100 as a weightlifting belt, the invention 100 may be worn with the abdominal plate 240 positioned over the abdomen of the front torso F of a user U and the pack 200 positioned over the lower torso back B of the user U with the strap 252 encircling the torso B, F of a user U to couple the abdominal plate 240 to the pack 200. The strap 252 may then be tightened by reposition the male buckle component 260 on the strap 252, the female buckle component 270 on the strap 252, or both. The foam support 226 within the pack 200 may cushion the lower torso back B of a user U.

To use the invention 100 as a shoulder pack, the strap 252 may pass over the shoulder S of a user U and under the opposing arm A with the pack 200 position over the shoulder blade and the abdominal plate resting on the chest C of a user U. The items may be placed into the one (1) or more storage pockets 230 and carried by the shoulder pack.

Figure 1:
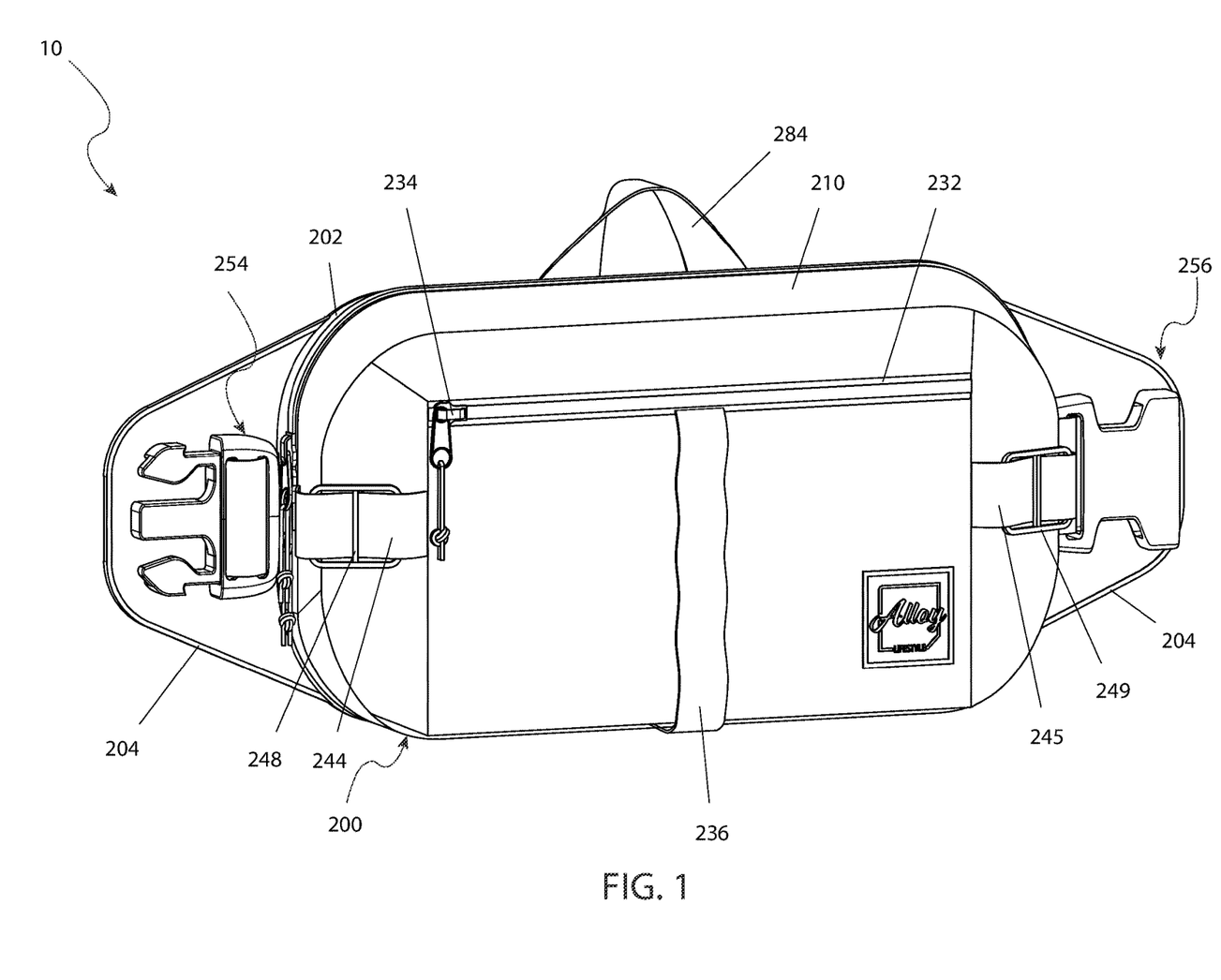
FIG. 1 is an isometric view of a weightlifting belt and shoulder pack assembly, according to an embodiment of the present invention.
Figure 2:
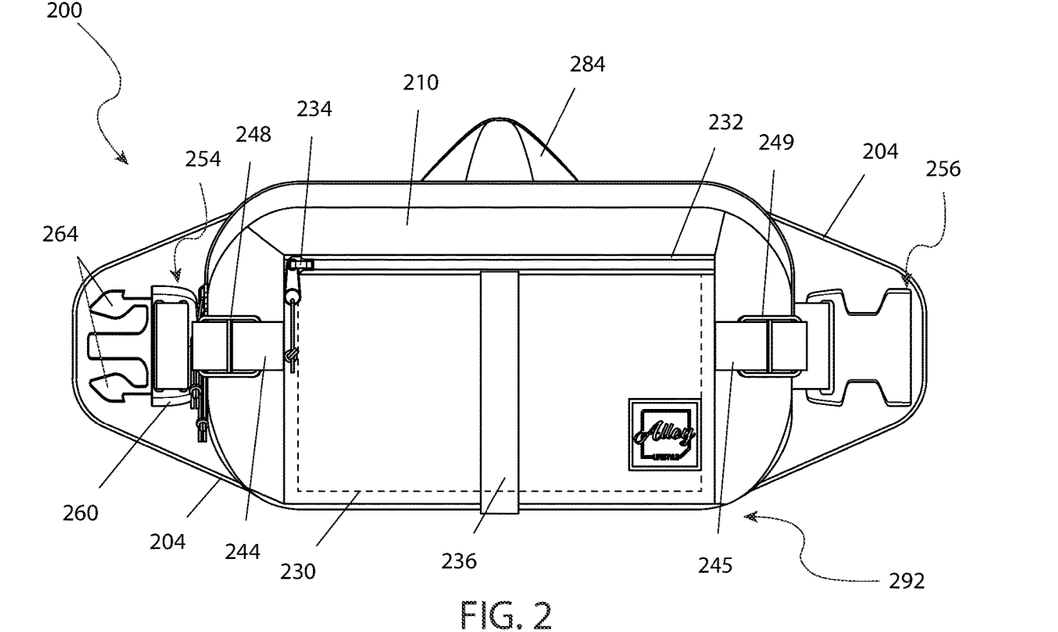
FIG. 2 is a non-contact side view of a pack, according to an embodiment of the present invention.
Figure 3:
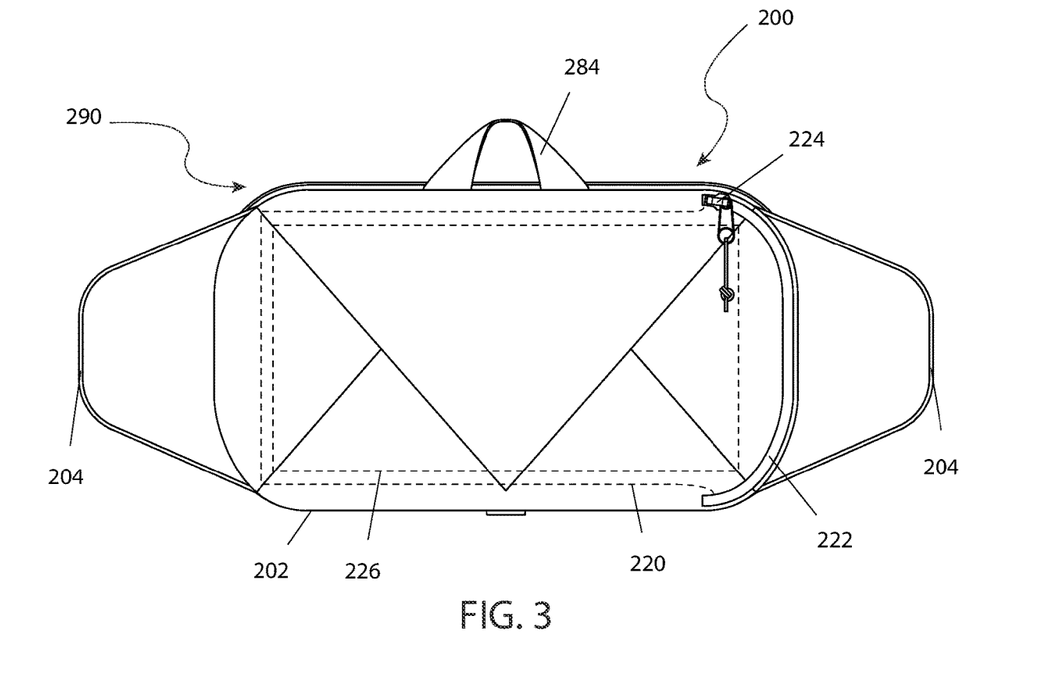
FIG. 3 is a contact side view of a pack, according to an embodiment of the present invention.
Figure 4:
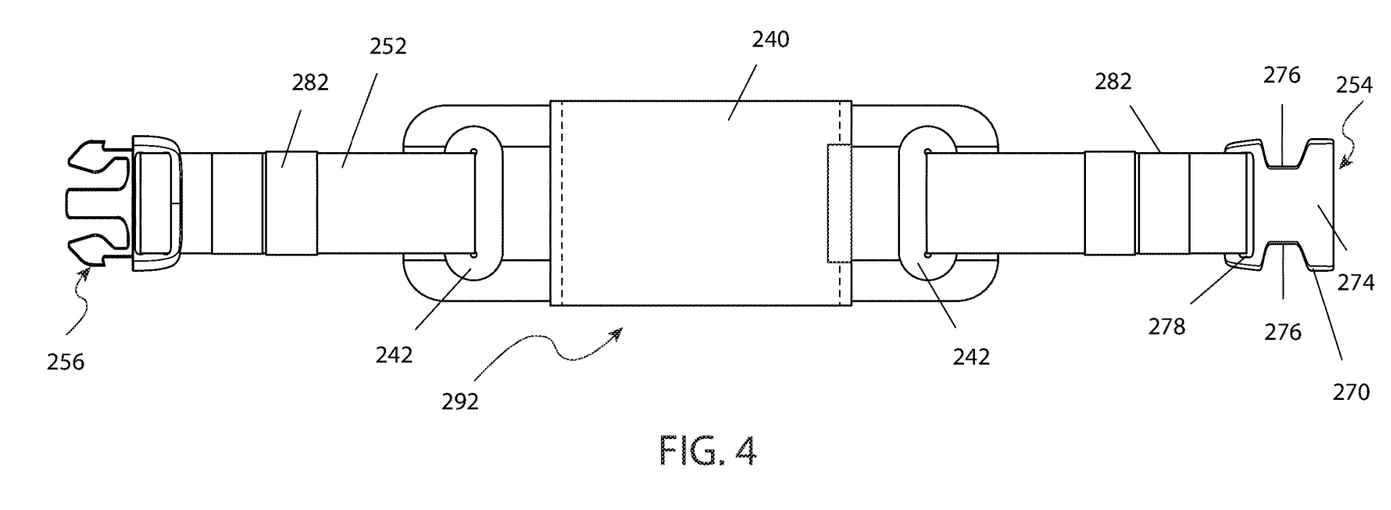
FIG. 4 is a non-contact side view of an abdominal plate and a strap, according to an embodiment of the present invention.
Figure 5:
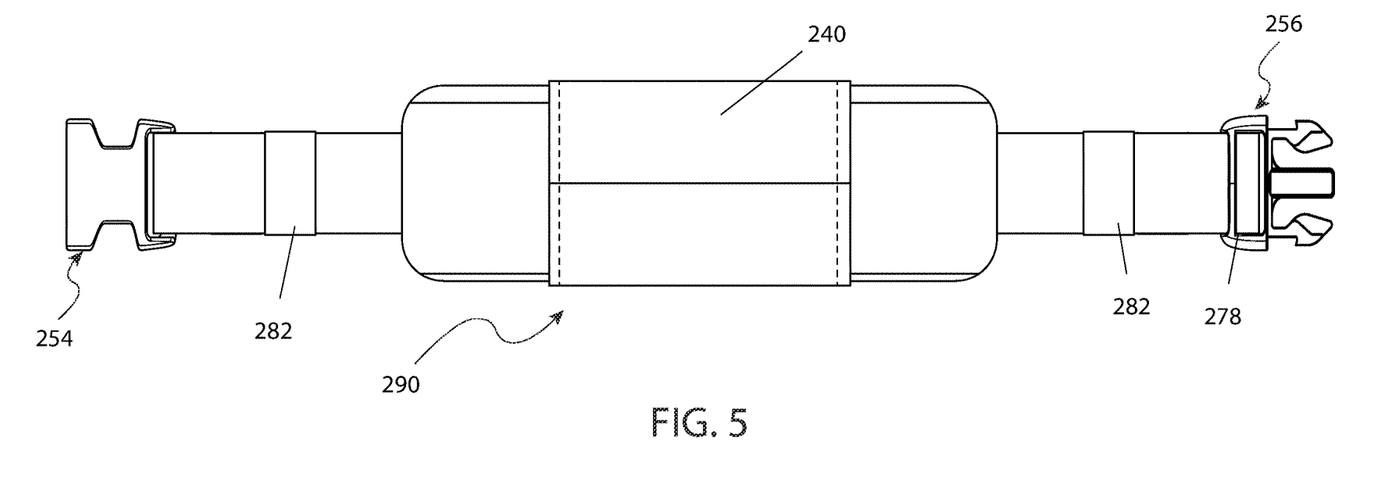
FIG. 5 is a contact side view of an abdominal plate and a strap, according to an embodiment of the present invention.

When the invention 100 is not in use, the strap 252 and be folded or wrapped around the abdominal plate 240 and the abdominal plate 240 and the strap 252 may be stored in one (1) of the storage pockets 230 (In FIG. 1, the abdominal strap 240 and the strap 252 are stored within the pack 200).

The exact specifications, materials used, and method of use of the invention 100 may vary upon manufacturing. The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A weightlifting belt and shoulder pack assembly, comprising:
   a pack having a panel and a pouch, wherein the panel includes a plurality of extension wings extending laterally beyond the pack, the extension wings adapted to flex and wrap partially around a torso of a user;
   an abdominal plate having a semi-rigid pad, the abdominal plate coupled to the pack;
   a strap made of flexible non-elastic material, the strap adapted to encircle the torso of the user to hold the abdominal plate in position at a torso front of the user and the pack in position at
   a lower torso back of the user;

a left buckle adapted to couple the strap to the pack on a left side of the user, the left buckle including a male buckle component and a female buckle component; and, a right buckle adapted to couple the strap to the pack on a right side of the user, the right buckle including a male buckle component and a female buckle component; and, wherein the pouch is a flexible bag removably coupled to the panel and includes a hollow interior adapted to hold a foam support and one or more items being carried.

2. The weightlifting belt and shoulder pack assembly of claim 1, wherein:

the foam support is inserted into and removed from a contact side pocket of the pack via a contact side aperture; and, the contact side aperture is closed using a contact side fastener to prevent the foam support from sliding out of the pack; and, the contact side pocket is accessible from a contact side of the pack when the pack is not being worn.

3. The weightlifting belt and shoulder pack assembly of claim 2, further comprising:

a first pack strap having a first pack strap adjuster extending away from a first end of the pouch; and, a second pack strap having a second pack strap adjuster extending away from a second end of the pouch.

4. The weightlifting belt and shoulder pack assembly of claim 3, wherein:

the left buckle and the right buckle are side-release buckles; each side-release buckle comprises two release tabs on the side of the male buckle component that engage two release apertures on the side of the female buckle component to lock the left buckle and the right buckle together; and, the male buckle component is inserted into a mating aperture on the female buckle component, with one or more release tabs on the male buckle component engaging with one or more release apertures on the female buckle component to prevent release; and, the male buckle component is detached by applying external pressure to the one or more release tabs and pulling the male buckle component and the female buckle component apart.

5. The weightlifting belt and shoulder pack assembly of claim 4, further comprising:

one or more storage pockets on the pouch, each storage pocket accessible from a non-contact side of the pack via a storage aperture; each storage aperture is closed using a storage fastener to prevent items from sliding out of the pack; and, a front strap of webbing material affixed to a front surface of a storage pocket to enable retention of a piece of auxiliary equipment for storage or transport; and, wherein the strap includes one or more webbing sliders to capture and retain a free end of the strap after it has passed through a buckle component and made a one hundred eighty-degree turn.

* * * * *